(12) United States Patent
Sakaguchi (10) Patent No.: US 9,766,208 B2
(45) Date of Patent: Sep. 19, 2017

(54) SENSOR, AND MONITORING SYSTEM

(71) Applicant: BRIDGESTONE CORPORATION, Tokyo (JP)

(72) Inventor: Toshiki Sakaguchi, Yokohama (JP)

(73) Assignee: BRIDGESTONE CORPORATION, Chuo-ku, Tokyo (JP)

( * ) Notice: Subject to any disclaimer, the term of this patent is extended or adjusted under 35 U.S.C. 154(b) by 0 days.

(21) Appl. No.: 15/109,492

(22) PCT Filed: Jan. 26, 2015

(86) PCT No.: PCT/JP2015/000328
§ 371 (c)(1),
(2) Date: Jul. 1, 2016

(87) PCT Pub. No.: WO2015/111418
PCT Pub. Date: Jul. 30, 2015

(65) Prior Publication Data
US 2016/0327517 A1    Nov. 10, 2016

(30) Foreign Application Priority Data

Jan. 27, 2014  (JP) .................................. 2014-012373

(51) Int. Cl.
*B65G 43/02* (2006.01)
*B65G 43/08* (2006.01)
(Continued)

(52) U.S. Cl.
CPC ............. *G01N 27/82* (2013.01); *B65G 15/34* (2013.01); *B65G 43/02* (2013.01); *B65G 43/08* (2013.01);
(Continued)

(58) Field of Classification Search
CPC .............................. B65G 43/02; B65G 43/08
(Continued)

(56) References Cited

U.S. PATENT DOCUMENTS 5,500,641 A * 3/1996 Roberts ..................... F16P 3/00
340/665
5,957,263 A * 9/1999 Espenschied .......... G01B 21/06
198/349.95

(Continued)

FOREIGN PATENT DOCUMENTS

CN          86104961 A      2/1987
CN          2430403 Y       5/2001
(Continued)

OTHER PUBLICATIONS

International Search Report for PCT/JP2015/000328 dated Mar. 17, 2015.

*Primary Examiner* — Douglas Hess
(74) *Attorney, Agent, or Firm* — Sughrue Mion, PLLC (57) ABSTRACT

A sensor and monitoring system that can prevent the accumulation of scraps of a transport object on the sensor are provided. A sensor 4 is located below a return-side portion 2a of a conveyor belt 2, and includes: a detector 40 that detects a detection object 3 embedded in the conveyor belt; and a cover 41 covering at least an upper part of the detector, wherein the cover has a downward surface 411 that extends continuously downward from a top part of the cover while extending outward in the horizontal direction.

8 Claims, 5 Drawing Sheets

(51) Int. Cl.
*G01N 27/82* (2006.01)
*B65G 15/34* (2006.01)
*B65G 45/00* (2006.01)

(52) U.S. Cl.
CPC ...... *B65G 45/00* (2013.01); *B65G 2203/0275* (2013.01); *B65G 2203/043* (2013.01)

(58) Field of Classification Search
USPC .......................................... 198/502.1, 502.3
See application file for complete search history.

(56) References Cited

U.S. PATENT DOCUMENTS

| | | | | |
|---|---|---|---|---|
| 6,837,363 | B2 * | 1/2005 | Munzebrock | G05B 9/03 198/502.1 |
| 8,627,946 | B2 * | 1/2014 | Baitz | G07G 1/0045 198/502.1 |
| 8,630,537 | B2 * | 1/2014 | Kadaba | G05B 19/0428 348/61 |
| 8,641,942 | B2 * | 2/2014 | Breuer | B29C 47/0016 264/40.1 |
| 8,851,268 | B2 * | 10/2014 | Kameda | A61F 13/15772 198/339.1 |
| 8,991,589 | B2 * | 3/2015 | Marcantoni | B65C 9/067 198/469.1 |
| 9,359,146 | B2 * | 6/2016 | Salice | B65G 43/00 |
| 9,440,799 | B1 * | 9/2016 | Wang | B65G 43/02 |
| 9,499,939 | B2 * | 11/2016 | Medoff | C10L 5/442 |
| 9,533,831 | B2 * | 1/2017 | Nelson | B65G 43/02 |
| 2004/0164826 | A1 | 8/2004 | Okumura | |

FOREIGN PATENT DOCUMENTS

| | | |
|---|---|---|
| CN | 102992000 A | 3/2013 |
| DE | 102008061729 A1 | 6/2010 |
| EP | 2500295 A1 | 9/2012 |
| JP | 11-079336 A | 3/1999 |
| JP | 11-301842 A | 11/1999 |
| JP | 2004-259455 A | 9/2004 |
| JP | 2011-69617 A | 4/2011 |
| WO | 2011/058755 A1 | 5/2011 |

* cited by examiner

SENSOR, AND MONITORING SYSTEM

CROSS REFERENCE TO RELATED APPLICATIONS

This application is a National Stage of International Application No. PCT/JP2015/000328 filed Jan. 26, 2015, claiming priority based on Japanese Patent Application No. 2014-012373 filed Jan. 27, 2014, the contents of all of which are incorporated herein by reference in their entirety.

TECHNICAL FIELD

The disclosure relates to a sensor and monitoring system used for a conveyor belt.

BACKGROUND

A conventionally known conveyor belt wear detection apparatus includes: a rubber magnet embedded in a conveyor belt; a magnetic sensor that is disposed below a front-side surface forming the outer peripheral surface of the conveyor belt, and detects a magnetic field from the rubber magnet; and an arithmetic section for estimating, based on a signal from the magnetic sensor, the amount of wear of the front-side surface of the conveyor belt (for example, Patent Literature (PTL) 1).

CITATION LIST

Patent Literature

PTL 1: WO 2011/058755 A1

SUMMARY

Technical Problem

With the technique mentioned above, the sensor is located below the front-side surface of the conveyor belt, on the return side of the conveyor belt. There is accordingly a possibility that scraps of a transport object adhering to the front-side surface of the conveyor belt accumulate on the sensor, and the scraps accumulated on the sensor gradually absorb moisture to solidify and harden. The sensor needs to be close to the conveyor belt, in order to have desired sensitivity. This raises concern that, for example when the conveyor belt vibrates, the scraps which have accumulated and hardened on the sensor come into contact with the conveyor belt and damage or wear the conveyor belt.

It could therefore be helpful to provide a sensor and monitoring system that can prevent the accumulation of scraps of a transport object on the sensor.

Solution to Problem

A sensor according to the disclosure is a sensor located below a return-side portion of a conveyor belt, the sensor including: a detector that detects a detection object embedded in the conveyor belt; and a cover covering at least an upper part of the detector, wherein the cover has a downward surface that extends continuously downward from a top part of the cover while extending outward in the horizontal direction.

With this structure, the accumulation of scraps of a transport object on the sensor can be prevented.

In the sensor, preferably, the cover includes: an outer cover; and an inner cover located inside the outer cover and covering the entire detector, and the outer cover has the downward surface that extends continuously downward from a top part of the outer cover while extending outward in the horizontal direction. With this structure, for example, the accumulation of scraps of a transport object on the outer cover can be prevented while protecting the detector from moisture, stains, etc. by the inner cover.

In the sensor, preferably, an outer shape of the inner cover has a substantially rectangular horizontal section. With this structure, the inner cover can be formed easily.

In the sensor, preferably, the inner cover has a housing space in which the detector and a detector-side end of an electric cable connected to the detector are housed without leaving any space substantially. With this structure, the entrance of foreign matter into the inner cover can be suppressed effectively.

In the sensor, preferably, an inner wall surface of the inner cover defining the housing space has, in a part surrounding the electric cable, an annular rib protruding toward an inner peripheral side of the electric cable. With this structure, the entrance of foreign matter into the inner cover can be suppressed more effectively.

The sensor preferably includes a plurality of detectors arranged in a width direction of the conveyor belt, as the detector, wherein the cover includes: a plurality of outer covers adjacent to each other in the width direction of the conveyor belt, as the outer cover; and a plurality of inner covers corresponding one-to-one to the plurality of detectors, as the inner cover, and each of the plurality of outer covers covers at least upper parts of two or more detectors of the plurality of detectors. With this structure, the strength of the outer cover can be enhanced, with it being possible to effectively prevent the breakage of the sensor.

A monitoring system according to the disclosure is a monitoring system for a conveyor belt, the monitoring system including: a detection object embedded in the conveyor belt; and a sensor located below a return-side portion of the conveyor belt, wherein the sensor includes: a detector that detects the detection object; and a cover covering at least an upper part of the detector, and the cover has a downward surface that extends continuously downward from a top part of the cover while extending outward in the horizontal direction.

With this structure, the accumulation of scraps of a transport object on the sensor can be prevented.

In the monitoring system, preferably, at least a part of the downward surface extends continuously downward from the top part of the cover toward a back side in a running direction of the return-side portion of the conveyor belt. With this structure, the impact when the sensor and the conveyor belt come into contact with each other can be reduced.

Advantageous Effect

It is thus possible to provide a sensor and monitoring system that can prevent the accumulation of scraps of a transport object on the sensor.

DETAILED DESCRIPTION

The following describes one of the disclosed embodiments with reference to drawings.

Figure 1:
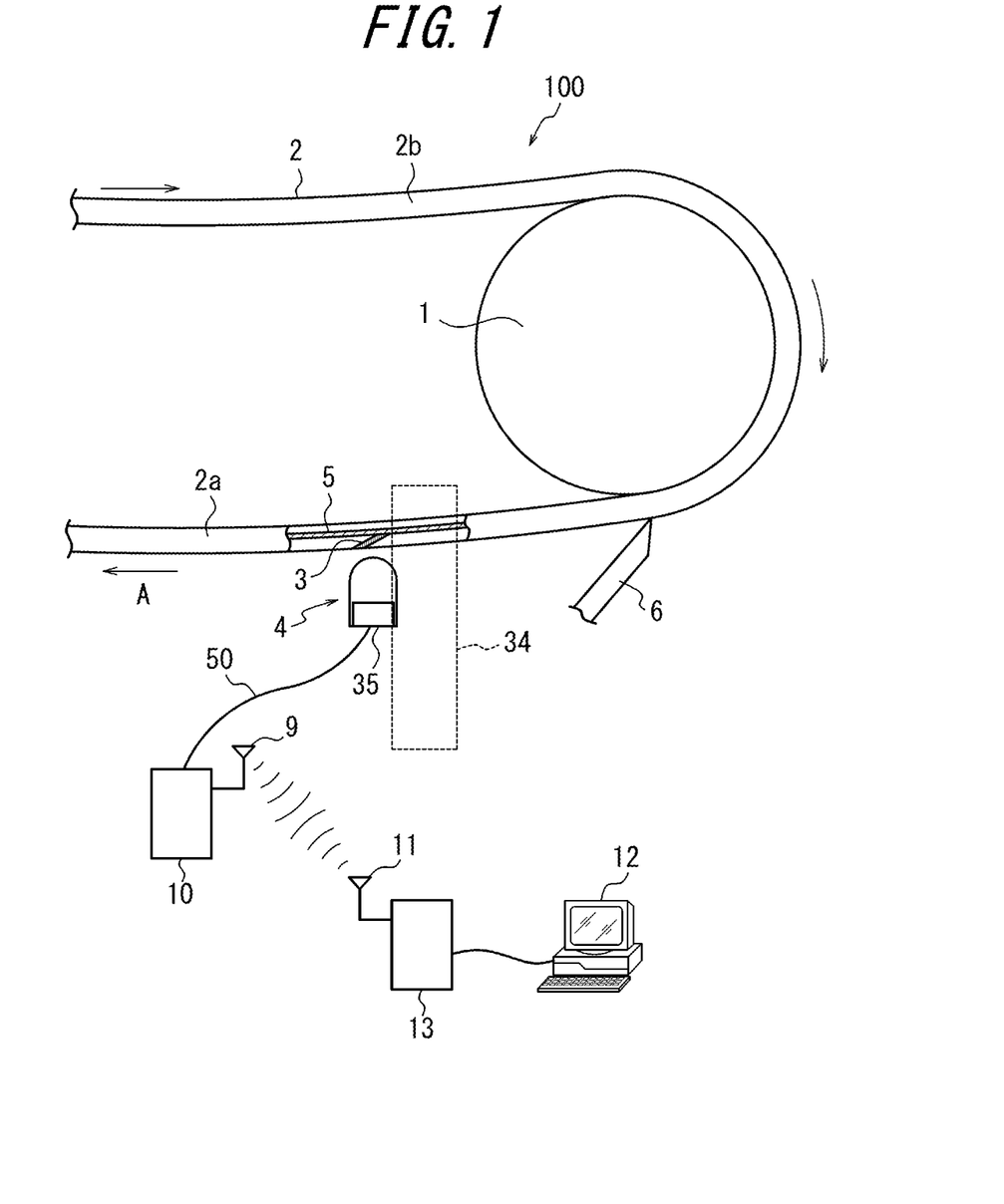
FIG. 1 is a side view illustrating an embodiment of a monitoring system according to the disclosure used for a conveyor belt.
Figure 2:
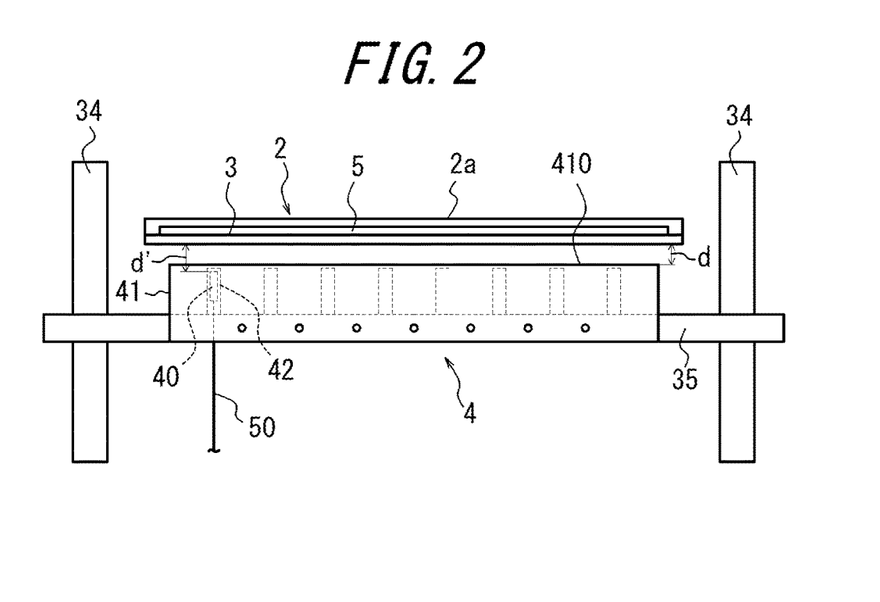
FIG. 2 is a front view illustrating the monitoring system in FIG. 1 used for the conveyor belt.

FIGS. 1 to 5 illustrate an embodiment of a monitoring system according to the disclosure. The monitoring system in this embodiment is a system for monitoring the state of wear of a conveyor belt. FIG. 1 is a side view illustrating a monitoring system 100 used for a conveyor belt 2, where a part of the conveyor belt 2 is illustrated in a cross section along the longitudinal direction of the conveyor belt 2 (hereafter also simply referred to as "belt longitudinal direction"). FIG. 2 is a front view of the monitoring system 100 as seen from the left side in FIG. 1, where the lower portion of the conveyor belt 2 is illustrated in a cross section along the width direction of the conveyor belt 2 (hereafter also simply referred to as "belt width direction"). The conveyor belt 2 is an annular belt wound around a pulley 1, and transports a transport object (iron ore, coal, etc.) on an upper carrier-side portion 2b of the vertically facing portions of the conveyor belt 2. The lower portion of the conveyor belt 2 is a return-side portion 2a not transporting the transport object.

The monitoring system 100 includes: a rubber magnet 3 (detection object) embedded in a rubber member of the conveyor belt 2; and a magnetic sensor 4 (sensor) located below the return-side portion 2a of the conveyor belt 2, near the end in the extension direction of the conveyor belt 2 in this example. The magnetic sensor 4 detects the magnetic field of the rubber magnet 3, when the rubber magnet 3 passes above the magnetic sensor 4 while the conveyor belt 2 is running. The monitoring system 100 monitors the wear state of the conveyor belt 2, based on a detection signal from the magnetic sensor 4. Here, "below the return-side portion 2a" means that at least a part of the magnetic sensor 4 (the entire magnetic sensor 4 in this example) is in a downward projection plane of the return-side portion 2a.

In the example illustrated in FIGS. 1 and 2, the rubber magnet 3 has a substantially planar shape. The rubber magnet 3 is inclined with respect to the horizontal direction across the full belt width, on the outer peripheral side of the conveyor belt 2 (hereafter also simply referred to as "belt outer peripheral side") relative to a reinforcing member 5 (steel cords or the like) extending around the entire circumference inside the rubber member of the conveyor belt 2. The end of the rubber magnet 3 on the belt outer peripheral side is in plane with the outer peripheral surface of the conveyor belt 2. The end of the rubber magnet 3 on the inner peripheral side of the conveyor belt 2 (hereafter also simply referred to as "belt inner peripheral side") is in contact with the reinforcing member 5, on the back side (the right side in FIG. 1) in the running direction A of the return-side portion 2a of the conveyor belt 2 (hereafter also simply referred to as "running direction A") relative to the end of the rubber magnet 3 on the belt outer peripheral side.

For example, the rubber magnet 3 may be obtained by magnetizing, in the thickness direction, a bond magnet that is molded in the shape of a sheet from a magnet powder dispersively mixed in a rubber matrix. Examples of the magnet powder include rare-earth magnets such as ferrite, neodymium-iron-boron, and samarium-iron-nitrogen, and alnico magnets.

In the example illustrated in FIG. 1, the magnetic sensor 4 is fixed to a sensor fixing frame 35 extending in the belt width direction, on the front side (the left side in FIG. 1) in the running direction A relative to a scraper 6 for scraping chips of the transport object transported by the carrier-side portion 2b of the conveyor belt 2. The structure of the magnetic sensor 4 will be described in detail later.

As illustrated in FIG. 2, too, both ends of the sensor fixing frame 35 in the belt width direction are fixed to a pair of conveyor frames 34 supporting the conveyor belt 2 on both sides in the belt width direction so as to be able to run. Thus, the sensor fixing frame 35 is held at a predetermined height from the ground.

As illustrated in FIG. 1, the monitoring system 100 in this example further includes: a local arithmetic control section 10 connected to the magnetic sensor 4 via an electric cable 50; and a central control section 13 located away from the local arithmetic control section 10 and capable of wirelessly communicating with the local arithmetic control section 10. The local arithmetic control section 10, having received a detection signal from the magnetic sensor 4, calculates the degree of wear of the conveyor belt 2 based on the received detection signal, and transmits the calculation result from a transmission section 9. The central control section 13 receives the signal from the local arithmetic control section 10 by a reception section 11, and performs various calculation based on the received signal. The central control section 13 outputs the calculation result to an output terminal 12 (such as a personal computer) and/or, in the case of determining that the degree of wear exceeds a predetermined threshold based on the calculation result, issues a warning or stops the conveyor belt 2.

The magnetic sensor 4 is described in more detail below. As illustrated in FIGS. 2 to 5A, the magnetic sensor 4 includes: one or more detectors 40 (eight detectors 40 in the illustrated example); a single outer cover 41 (cover) covering at least the upper parts of all detectors 40 (the upper and side parts except the lower parts in this example); and one or more inner covers 42 (cover) (eight inner covers 42 in the illustrated example) located inside the outer cover 41 and each covering a different one of the detectors 40 entirely.

Figure 3:
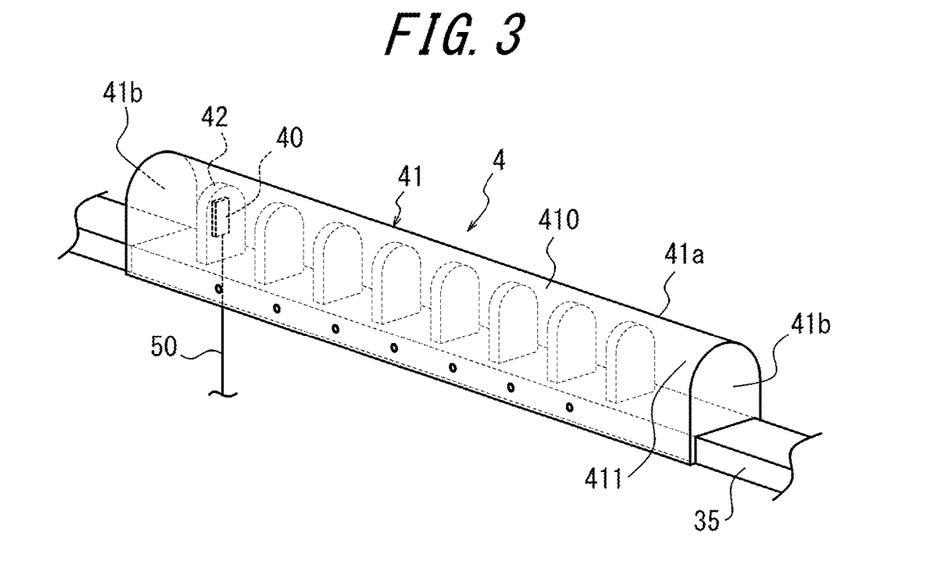
FIG. 3 is a perspective view illustrating the sensor in FIG. 1 fixed to a sensor fixing frame.

Each detector 40 is composed of an electronic circuit board of a magnetic inductive (MI) sensor, Hall sensor, loop coil sensor, or the like, and has a function of detecting the rubber magnet 3 in the magnetic sensor 4. As illustrated in FIG. 2, the detectors 40 are arranged at regular intervals (for example, 100 mm) in the belt width direction so that each detector 40 does not affect the sensitivity of the other detectors 40. A detection signal from each detector 40 is output to the local arithmetic control section 10 via the corresponding electric cable 50. The monitoring system 100 determines, based on the output waveform obtained from each detector 40, the wear state of the conveyor belt 2 in the belt width direction position corresponding to the detector 40. In FIGS. 2 and 3, only the detector 40 housed in one inner cover 42 and the electric cable 50 connected to the detector 40 are illustrated and the detectors 40 and electric cables 50 corresponding to the other inner covers 42 are omitted for simplicity's sake.

Each inner cover 42 is made of, for example, a resin such as polycarbonate, and seals the detector 40 to protect the detector 40 from moisture and stains. The inner cover 42 has a substantially planar shape. In more detail, the outer shape of the inner cover 42 has a substantially rectangular horizontal section (a rectangle which is longer in the belt longitudinal direction and shorter in the belt width direction in the illustrated example).

The upper surface of the inner cover 42 is curved like an upward convex arc in a virtual plane including the belt longitudinal direction and the vertical direction, and has a shape that extends this curved shape along the belt width direction.

The bottom surface of the inner cover 42 is located on the upper surface of the sensor fixing frame 35, and the upper end of the inner cover 42 is close to or in contact with the inner surface of the outer cover 41 (in contact with the inner surface in the illustrated example). In this example, the electric cable 50 extends downward from the lower end of the detector 40 inside the inner cover 42 and comes out of the inner cover 42 from the bottom surface of the inner cover 42, and further extends downward through an opening (not illustrated) formed in the sensor fixing frame 35.

Figure 4:
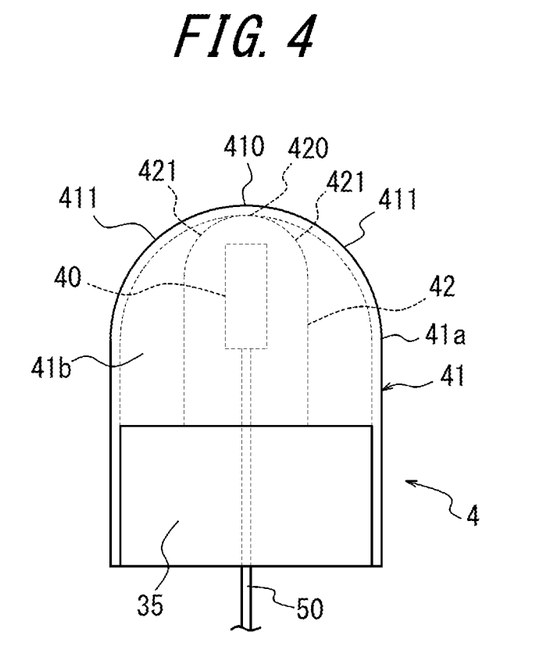
FIG. 4 is a side view illustrating the sensor in FIG. 1 fixed to the sensor fixing frame.
Figure 5A:
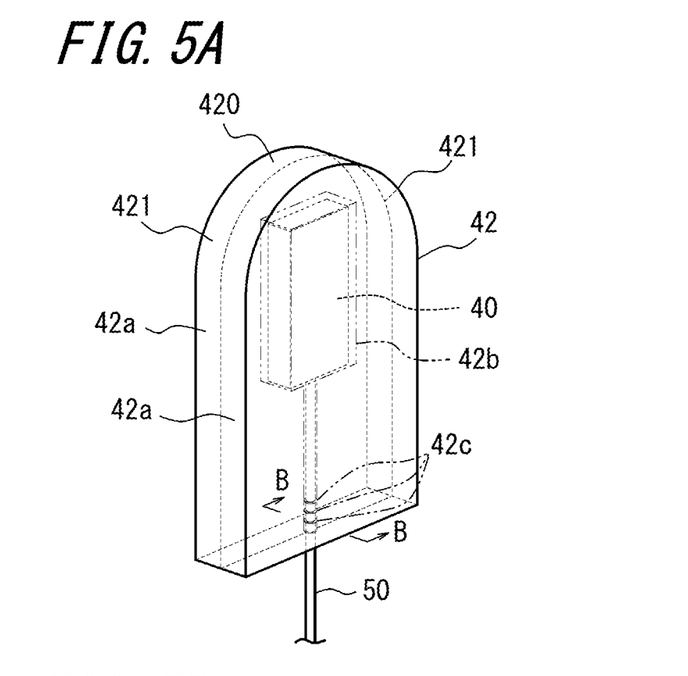
FIG. 5A is a perspective view illustrating a detector and an inner cover in FIG. 4.

As illustrated in FIG. 5A, the inner cover 42 in this example is formed by bonding a pair of panels 42a facing each other in its width direction (the direction perpendicular to the plane of paper in FIG. 4, i.e. the belt width direction) by ultrasonic welding or the like in the state of housing the detector 40 inside. In the state where the pair of panels 42a are bonded together, the inner cover 42 forms a housing space in which the detector 40 and the end of the electric cable 50 on the inner cover 42 side are housed without leaving any space substantially. In other words, the inner wall surface 42b of the inner cover 42 defining the housing space has a shape approximately coinciding with the detector 40 and the end of the electric cable 50 on the inner cover 42 side, but is slightly larger in size than these parts. Accordingly, in the state where the detector 40 and the end of the electric cable 50 on the inner cover 42 side are housed in the inner cover 42, approximately no air is present in the inner cover 42, and the detector 40 and the end of the electric cable 50 on the inner cover 42 side are substantially embedded in the material (such as a resin) forming the inner cover 42. This effectively prevents foreign matter such as dust from entering the inner cover 42 and adhering to the detector 40. Moreover, in the case where the outer shape of the inner cover 42 has a substantially rectangular horizontal section as in this example, the formation of the inner cover 42 and therefore the manufacture of the magnetic sensor 4 are easier than in the case where, for example, the outer shape has a substantially circular horizontal section.

Figure 5B:
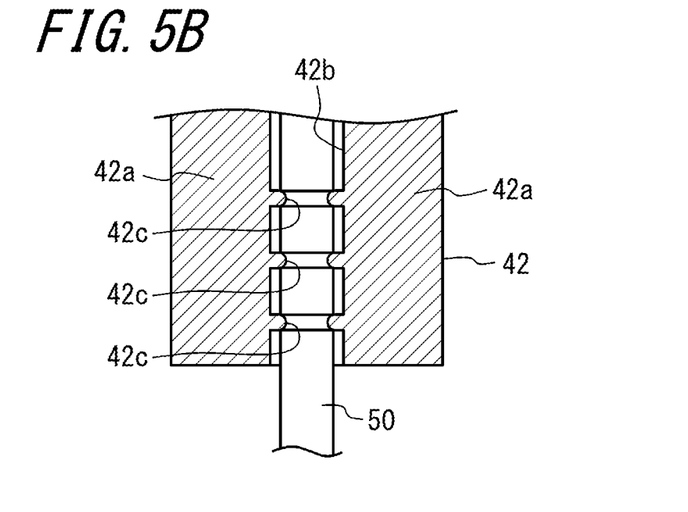
FIG. 5B is a main part sectional view of the inner cover along line B-B in FIG. 5A.

FIG. 5B is a vertical sectional view of the inner cover 42 and the electric cable 50 along line B-B in FIG. 5A. In this example, the inner wall surface 42b of the inner cover 42 defining the housing space has, in its lower part surrounding the electric cable 50, one or more annular ribs 42c protruding toward the inner peripheral side of the electric cable 50, as illustrated in FIG. 5B. In this example, a plurality of (more specifically, three) annular ribs 42c are formed away from each other in the vertical direction. The inner diameter of each annular rib 42c is smaller than the outer diameter of the electric cable 50. Such annular ribs 42c dig into the electric cable 50, in the state where the electric cable 50 is housed in the housing space of the inner cover 42. Thus, the provision of the annular ribs 42c further ensures that the detector 40 and the end of the electric cable 50 on the inner cover 42 side are sealed in the inner cover 42 to keep foreign matter from entering the inner cover 42.

The outer cover 41 is made of, for example, a resin such as PET, or FRP. The outer cover 41 includes: a cover plate portion 41a extending in the belt width direction along most of the conveyor belt 2 in the belt width direction, and bent substantially in the shape of inverted U so as to straddle the sensor fixing frame 35 and the inner cover 42 in the belt longitudinal direction, with the lower ends on both sides in the belt longitudinal direction being fixed to the sensor fixing frame 35; and a pair of end plate portions 41b closing the gap between the upper surface of the sensor fixing frame 35 and the substantially inverted U-shaped edges of the cover plate portion 41a on both sides in the belt width direction.

The cover plate portion 41a and the pair of end plate portions 41b may be formed separately and fixed to each other by adhesion or the like, or formed integrally.

By covering at least the upper parts of all inner covers 42 (and therefore at least the upper parts of all detectors 40) with the outer cover 41 as in this example, scraps of the transport object falling from the outer surface of the return-side portion 2a of the conveyor belt 2 can be kept from accumulating between the inner covers 42 (and therefore between the detectors 40).

The upper surface of the outer cover 41 is curved like an upward convex arc in the virtual plane including the belt longitudinal direction and the vertical direction, and has a shape that extends this curved shape along the belt width direction. The outer cover 41 therefore has a downward surface 411 that extends continuously downward from the top part 410 (upper end) of the outer cover 41 toward the horizontal outside (both sides in the belt longitudinal direction in this example). In the case where the outer cover 41 has the downward surface 411, even when scraps of the transport object adhering to the outer surface of the return-side portion 2a of the conveyor belt 2 fall on the outer cover 41, the scraps are likely to slide along the downward surface 411 and fall to the ground. This prevents the accumulation of scraps on the magnetic sensor 4, and thus protects the conveyor belt from damage or wear caused by such scraps.

Here, "extending continuously downward" means that the downward surface 411 extends downward, without ever extending along the horizontal direction. This includes not only the case where the downward surface 411 extends downward in the shape of a convex arc protruding upward as in this example, but also the case where the downward surface 411 extends downward in the shape of a concave arc protruding downward, the case where the downward surface 411 extends downward in the shape of a curve while changing the radius of curvature of the curve or switching between extending along a convex arc protruding upward and extending along a concave arc protruding downward, the case where the downward surface 411 extends downward while extending linearly and inclined with respect to the horizontal direction and the vertical direction (where the inclination may change one or more times during the extending), etc. For example, in the case where the upper surface of the outer cover 41 has the downward surface 411 that linearly extends downward from the top part 410 of the outer cover 41 toward both sides in the belt longitudinal direction, the upper surface of the outer cover 41 is substantially triangular in the virtual plane including the belt longitudinal direction and the vertical direction. The accumulation of scraps on the magnetic sensor 4 can be prevented in such a case, too.

The accumulation of scraps on the magnetic sensor 4 can be prevented as long as the downward surface 411 extends continuously downward from the top part 410 of the outer cover 41 toward the horizontal outside. For example, in addition to or instead of this example, the downward surface 411 may extend continuously downward from the top part 410 toward the outside in the belt width direction, on both sides of the outer cover 41 in the belt width direction.

To prevent the accumulation of scraps on the magnetic sensor 4, the upper surface of the outer cover 41 preferably does not include a flat surface along the horizontal direction or a concave surface protruding downward.

In this example, at least a part of the downward surface 411 (a part of the downward surface 411 in the illustrated example) extends continuously downward from the top part 410 of the outer cover 41 toward the back side in the running direction A. This not only prevents the accumulation of scraps on the magnetic sensor 4, but also reduces the impact when the magnetic sensor 4 (more specifically, the outer cover 41) and the return-side portion 2a of the conveyor belt 2 come into contact with each other during the vibration of the conveyor belt 2 or the like. Hence, the breakage of the magnetic sensor 4 can be prevented.

To reduce the impact at the time of contact between the outer cover 41 and the return-side portion 2a of the conveyor belt 2, the part of the downward surface 411 from the top part 410 of the outer cover 41 to the back side in the running direction A is preferably curved smoothly in the belt longitudinal direction as in this example.

In the illustrated example, in the virtual plane including the belt longitudinal direction and the vertical direction, the radius of curvature (for example, 40 mm) of the arc-shaped inner surface (lower surface) of the cover plate portion 41a of the outer cover 41 is greater than or equal to the radius of curvature (for example, 20 mm) of the arc-shaped upper surface of the inner cover 42, as illustrated in FIG. 4. This enables the upper end of the inner cover 42 to be in contact with or sufficiently close to the upper end of the inner surface of the cover plate portion 41a of the outer cover 41 (in contact with the upper end of the inner surface of the cover plate portion 41a in the illustrated example). Meanwhile, the vertical distance d between the top part 410 of the outer cover 41 and the outer surface of the return-side portion 2a of the conveyor belt 2 is as small as possible (for example, 20 mm) within the range where the two parts do not come into contact with each other due to slight vibration which can typically occur in the conveyor belt 2. With such a structure, the vertical distance d' between the upper end of each detector 40 and the outer surface of the return-side portion 2a of the conveyor belt 2 is sufficiently small (for example, 30 mm), enabling the detector 40 to exhibit sufficient ability to detect the rubber magnet 3.

Here, the inner cover 42 may be omitted so that each detector 40 is covered only with the single outer cover 41. In this case, the vertical distance d' between the upper end of each detector 40 and the outer surface of the return-side portion 2a of the conveyor belt 2 can be further reduced.

Alternatively, the outer cover 41 may be omitted so that each detector 40 is covered only with the corresponding inner cover 42. In this case, if each inner cover 42 has a downward surface 421 that extends continuously downward from the top part 420 of the inner cover 42 toward the horizontal outside (both sides in the belt longitudinal direction in the illustrated example) as illustrated in FIGS. 4 and 5A, the accumulation of scraps on the inner cover 42 and therefore on the magnetic sensor 4 can be prevented. Moreover, if at least a part of the downward surface 421 of the inner cover 42 (a part of the downward surface 421 in the illustrated example) extends continuously downward from the top part 420 of the inner cover 42 toward the back side in the running direction A as in the illustrated example, the impact when the inner cover 42, i.e. the magnetic sensor 4, and the return-side portion 2a of the conveyor belt 2 come into contact with each other during the vibration of the conveyor belt 2 or the like can be reduced.

Figure 6:
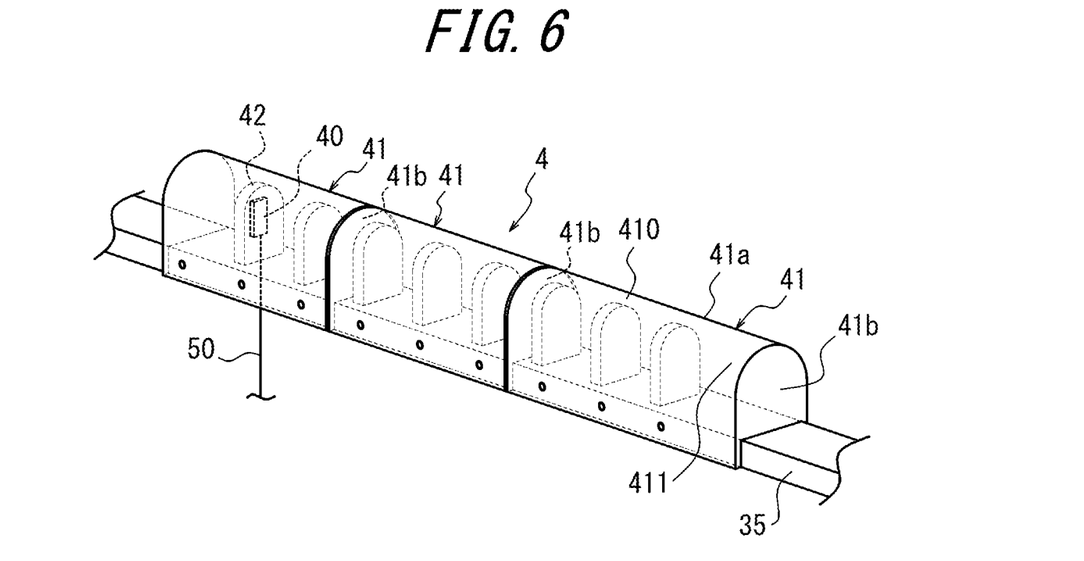
FIG. 6 is a perspective view illustrating a modification of an outer cover.

In the case where the magnetic sensor 4 includes a plurality of detectors 40 arranged in the width direction of the conveyor belt, these detectors 40 may be covered with a plurality of outer covers 41 adjacent to each other in the width direction of the conveyor belt 2, as in a modification illustrated in FIG. 6. In this case, each outer cover 41 covers at least the upper parts of two or more detectors 40 (preferably, two or three detectors 40). In the example in FIG. 6, the eight detectors 40 in the magnetic sensor 4 are covered with the respective inner covers 42, and also covered with the three outer covers 41 adjacent to each other in the width direction of the conveyor belt 2. Here, each outer cover 41 covers two or three detectors 40. By covering the plurality of detectors 40 in the magnetic sensor 4 with the plurality of outer covers 41 as in this example, the strength of each outer cover 41 is enhanced as compared with the case where the plurality of detectors 40 are covered with the single outer cover 41 as in the example in FIG. 3. This more effectively prevents the breakage of the outer cover 41 and therefore the breakage of the magnetic sensor 4, when the outer cover 41 and the return-side portion 2a of the conveyor belt 2 come into contact with each other during the vibration of the conveyor belt 2 or the like.

INDUSTRIAL APPLICABILITY

The disclosed technique may be used, for example, for a sensor and monitoring system for monitoring the state of wear of a conveyor belt.

REFERENCE SIGNS LIST 1 pulley
2 conveyor belt
2a return-side portion
2b carrier-side portion
3 rubber magnet
4 magnetic sensor (sensor)
5 reinforcing member
6 scraper
9 transmission section
10 local arithmetic control section
11 reception section
12 output terminal
34 conveyor frame
35 sensor fixing frame
40 detector
41 outer cover (cover)
41a cover plate portion
41b end plate portion
42 inner cover (cover)
42a panel
50 electric cable
100 monitoring system
410 top part
411 downward surface
420 top part
421 downward surface
A running direction of return-side portion

The invention claimed is:

1. A sensor located below a return-side portion of a conveyor belt, the sensor comprising:
   a detector that detects a detection object embedded in the conveyor belt; and
   a cover covering at least an upper part of the detector,
   wherein the cover has a downward surface that extends continuously downward from a top part of the cover while extending outward in a horizontal direction,
   the top part of the cover is distanced from the return-side portion of the conveyor belt, such that the cover does not come into contact with the belt when the belt vibrates.

2. The sensor according to claim 1,
   wherein the cover includes: an outer cover; and an inner cover located inside the outer cover and covering the entire detector, and
   the outer cover has the downward surface that extends continuously downward from a top part of the outer cover while extending outward in the horizontal direction.

3. The sensor according to claim 2,
   wherein an outer shape of the inner cover has a substantially rectangular horizontal section.

4. The sensor according to claim 2,
   wherein the inner cover has a housing space in which the detector and a detector-side end of an electric cable connected to the detector are housed while leaving substantially no space.

5. The sensor according to claim 4,
   wherein an inner wall surface of the inner cover defining the housing space has, in a part surrounding the electric cable, an annular rib protruding toward an inner peripheral side of the electric cable.

6. The sensor according to claim 2, further comprising a plurality of the detectors arranged in a width direction of the conveyor belt,
   wherein the cover includes: a plurality of the outer covers adjacent to each other in the width direction of the conveyor belt; and a plurality of the inner covers, each inner cover being provided for each detector, and
   each of the plurality of outer covers covers at least upper parts of two or more detectors of the plurality of detectors.

7. A monitoring system for a conveyor belt, the monitoring system comprising:
   a detection object embedded in the conveyor belt; and
   a sensor located below a return-side portion of the conveyor belt,
   wherein the sensor includes:
   a detector that detects the detection object; and
   a cover covering at least an upper part of the detector, and
   the cover has a downward surface that extends continuously downward from a top part of the cover while extending outward in the horizontal direction,
   the top part of the cover is distanced from the return-side portion of the conveyor belt, such that the cover does not come into contact with the belt when the belt vibrates.

8. The monitoring system according to claim 7,
   wherein at least a part of the downward surface extends continuously downward from the top part of the cover toward a back side in a running direction of the return-side portion of the conveyor belt.

* * * * *